(12) United States Patent
Lee et al.

(10) Patent No.: US 11,915,813 B2
(45) Date of Patent: Feb. 27, 2024

(54) MEDICATION COMPLIANCE MANAGEMENT METHOD

(71) Applicant: JUBILEE BIOTECH CO., LTD., Wonju-si (KR)

(72) Inventors: Sung Kyoung Lee, Seoul (KR); Goonghyun Han, Siheung-si (KR)

(73) Assignee: JUBILEE BIOTECH CO., LTD., Wonju-si (KR)

( * ) Notice: Subject to any disclaimer, the term of this patent is extended or adjusted under 35 U.S.C. 154(b) by 259 days.

(21) Appl. No.: 17/547,161

(22) Filed: Dec. 9, 2021

(65) Prior Publication Data
US 2023/0187046 A1    Jun. 15, 2023

(51) Int. Cl.
| | | |
|---|---|---|
| G16H 20/17 | (2018.01) | |
| A61M 37/00 | (2006.01) | |
| G16H 70/40 | (2018.01) | |

(52) U.S. Cl.
CPC ........ *G16H 20/17* (2018.01); *A61M 37/0015* (2013.01); *G16H 70/40* (2018.01); *A61M 2037/0023* (2013.01); *A61M 2037/003* (2013.01); *A61M 2205/123* (2013.01); *A61M 2209/088* (2013.01)

(58) Field of Classification Search
CPC ........ G16H 20/17; G16H 70/40; G16H 10/60; G16H 40/63; G16H 40/67; G16H 20/10; G16H 80/00; A61M 37/0015; A61M 2037/0023; A61M 2037/003; A61M 2205/123; A61M 2209/088; A61M 2037/0061; A61M 2205/3584; A61M 2205/3592; A61M 2205/52
See application file for complete search history.

(56) References Cited

U.S. PATENT DOCUMENTS

| | | | |
|---|---|---|---|
| 8,668,675 B2 | 3/2014 | Chase et al. | |
| 11,090,434 B2 | 8/2021 | O'Connor et al. | |
| 2010/0121271 A1* | 5/2010 | Perriere | A61M 37/0015 604/110 |
| 2014/0276552 A1* | 9/2014 | Nguyen, Jr. | A61M 5/1723 705/2 |

FOREIGN PATENT DOCUMENTS

| | | | | |
|---|---|---|---|---|
| AU | 2002312013 A1 * | 12/2002 | ......... | A61B 5/14514 |
| WO | 2021/167410 A1 | 8/2021 | | |

OTHER PUBLICATIONS

Breland, Burnis D. "Continuous quality improvement using intelligent infusion pump data analysis." American Journal of Health-System Pharmacy 67.17: 1446(10). American Society of Health-System Pharmacists. (Sep. 1, 2010) (Year: 2010).*

* cited by examiner

*Primary Examiner* — Linh Giang Le
(74) *Attorney, Agent, or Firm* — Rabin & Berdo, P.C.

(57) ABSTRACT

Disclosed is a drug compliance management method including a microneedle applicator configured to infuse a drug by means of a microneedle in the form of a wearable device, a patient terminal configured to process drug compliance information including drug infusion information received from the microneedle applicator and medication information separately input by a patient after administration, a server configured to transmit the drug compliance information received from the patient terminal, and an expert terminal configured to display drug compliance information collected from a plurality of patient terminals.

7 Claims, 5 Drawing Sheets

MEDICATION COMPLIANCE MANAGEMENT METHOD

BACKGROUND

1. Field

The present disclosure relates to a method for managing medication compliance and, more particularly, to a method for managing medication compliance in association with drug infusion through a microneedle.

2. Discussion of Related Art

Recently, the importance of medication compliance is increasing. Medication compliance refers to the extent to which a patient takes a prescribed amount of medication on schedule according to a doctor's prescription, and it is known that only about 25-30% of all patients take their medications as prescribed.

Also, in reality, about ⅓ of all the patients do not remember exactly whether they took their medication during treatment periods, and about ½ of all the patients forget to take their medication.

According to a report by the American Pharmacists Association (APhA), 125,000 people die as a direct cause of medication non-compliance every year in the United States, and the cost is estimated to reach 360 trillion won (300 billion dollars) per year.

In order to solve such a problem and increase medication compliance, many mobile phone applications for managing a patient's medication have been released. Typical applications include Medisafe, MyTherapy, etc. Although the main function of these applications is to inform a patient so that he or she can take medication on schedule, there is an inconvenience in that the patient has to input a drug which is to be taken, a time when a drug should be taken, etc. by himself or herself. In addition, it is impossible for medical staff to monitor data, such as a patient's medication history, in real time or remotely.

Another way to increase medication compliance is an insulin pump, for example. Insulin pumps, such as Insulet Corporation's OMNIPOD, allow insulin to be infused continuously for several days or by a patient's manipulation while a needle is inserted into the patient's body.

As disclosed in U.S. Pat. No. 11,090,434, the insulin pump can provide biometric information and drug infusion amount information measured by a sensor (e.g., a continuous glucose monitor) to hospitals, health care companies, or services.

Recently, a method of infusing a drug through a microneedle has been in the spotlight, and most microneedles are manufactured such that they can be attached to skin as an adhesive patch.

Meanwhile, as in U.S. Pat. No. 8,668,675, if necessary, a hollow type microneedle may be inserted into skin to infuse a drug. However, such patch-type and hollow-type microneedles are mainly used for one-time use, and there is a problem in that periodic or repeated infusion is impossible. In order to solve this problem, the present applicant has disclosed a micro-needle applicator and a cartridge capable of periodically infusing a drug using a micro-needle through International Patent Publication WO2021/167410.

However, in order to more efficiently operate a microneedle applicator capable of periodically or repeatedly infusing a drug, there is a need for a method capable of managing compliance with drug infusion.

SUMMARY

The present disclosure is directed to providing a management method for periodically or repeatedly infusing a drug through a microneedle and managing drug compliance with respect to drug infusion.

The present disclosure is also intended to allow drug registration and compliance management to be performed by medical staff.

The present disclosure is also intended to record and store a failure cause or the like when drug infusion or medication administration fails.

The present disclosure is also intended to prevent infection of an insertion site due to the repeated insertion of a microneedle.

Hereinafter, the present disclosure will be described in more detail with reference to the drawings according to embodiments thereof.

According to an aspect of the present disclosure, there is provided a drug compliance management method including registering information on a patient and an expert in a server; issuing and inputting the expert's prescription to a patient terminal; preparing a cartridge including a plurality of through holes, a micro-needle base positioned in each of the through holes, and a microneedle formed on a lower surface of the microneedle base to deliver a drug according to the prescription; mounting the cartridge on the microneedle applicator; delivering the prescription from the cartridge or the patient terminal to the microneedle applicator; enabling a pressing portion of the microneedle applicator to operate every predetermined time according to the prescription to insert the microneedle into skin and infuse a drug; delivering a result of infusing the drug from the microneedle applicator to the patient terminal; when there is a separate prescription other than the prescription for the microneedle, inputting a type, a dose, and a medication cycle of a drug to be taken to the patient terminal according to the separate prescription and inputting whether to take medication according to the medication cycle; delivering, to the server, drug compliance information including infusion information of the drug infused by the micro-needle and collected by the patient terminal and medication information corresponding to the separate prescription; allowing the server to deliver the drug compliance information delivered from the patient terminal to an expert terminal; and allowing the expert terminal to classify and display drug compliance on the basis of the same drug.

When the infusion of the drug fails, a controller of the microneedle applicator may transmit a cause of the failure to the patient terminal, input the cause through the patient terminal when the patient does not take the drug according to the separate prescription, and add the cause to the drug compliance information.

The information of the patient may include the patient's name, age, and gender as essential information and may optionally include the patient's height and weight, the names of substances that cause an allergic reaction in the patient, and a medication history.

A disinfectant solution may be stored in some of a plurality of through holes in which the top and bottom are sealed by a thin film and in which the microneedle base is disposed, and when the thin film of the through hole in which the disinfecting solution is stored is damaged by the microneedle, the disinfecting solution may flow out to a site where the microneedle is inserted.

The microneedle may be pressed after the degree of adhesion to the skin is checked by an adhesion measurement unit of the microneedle applicator.

The drug compliance management method may further include allowing the microneedle applicator to notify the patient of the start of insertion either by itself or through the patient terminal before the microneedle is inserted.

The microneedle base may be pressed after a notification confirmation input is input to the patient terminal or the microneedle applicator.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
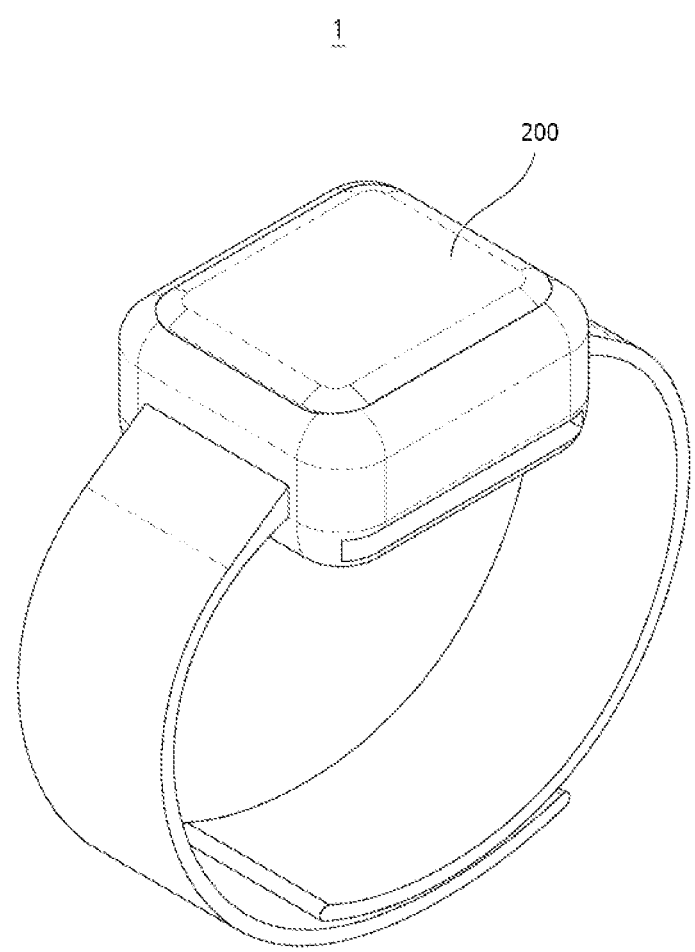
FIG. 1 is a view showing the appearance of a microneedle applicator in an embodiment of the present disclosure.
Figure 2:
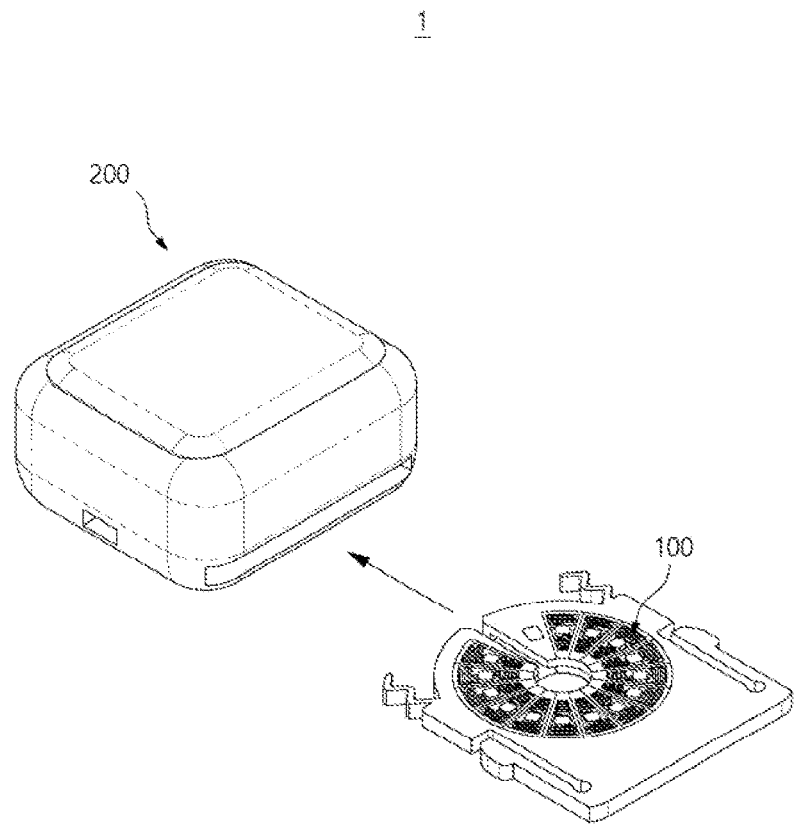
FIG. 2 is a view showing a microneedle applicator and a cartridge according to an embodiment of the present disclosure.
Figure 3:
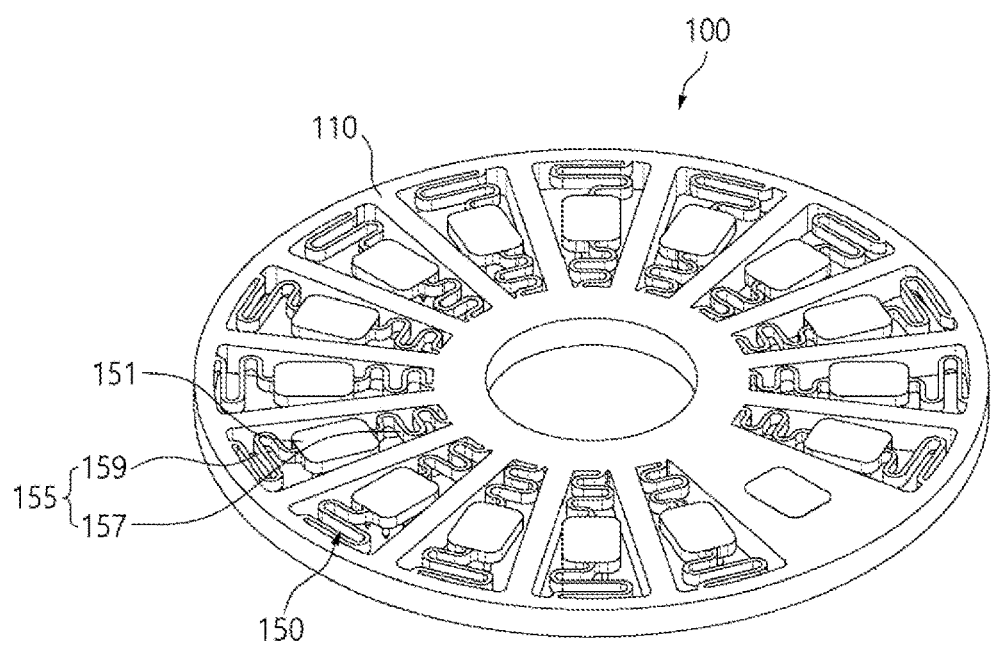
FIG. 3 is a view illustrating an upper configuration of a cartridge according to an embodiment of the present disclosure.
Figure 4:
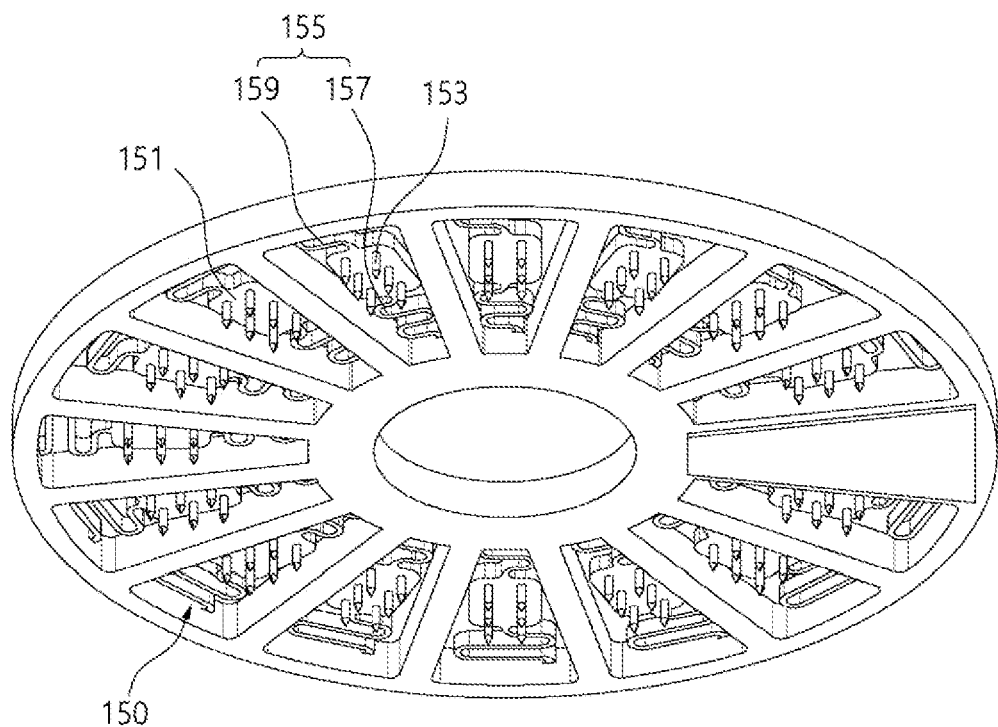
FIG. 4 is a view illustrating a lower configuration of a cartridge according to an embodiment of the present disclosure.

Hereinafter, the present disclosure will be described in more detail with reference to the drawings according to embodiments thereof.

The present disclosure includes a microneedle applicator 1 formed as a wearable device capable of infusing a drug by means of a microneedle, a patient terminal 2 configured to process drug compliance information including drug infusion information received from the microneedle applicator 1 and medication information separately input by a patient after administration, a server 3 configured to transmit to an expert terminal 4 the drug compliance information received from the patient terminal 2, and the expert terminal 4 configured to display drug compliance information collected from a plurality of patient terminals.

The microneedle applicator 1 may be a wearable device in the form of a wristwatch worn on a wrist or in the form of a band worn on body parts such as a forearm, a thigh, and a waist.

The microneedle applicator 1 is not limited to that for humans and may be used to infuse drugs into animals. For example, a microneedle applicator may be produced as a wearable device in the form of a necklace worn on the neck of an animal. The drug compliance management system and method of the present disclosure are not limited to humans.

A cartridge 100 having a plurality of microneedle bases 151 installed thereon is mounted on a main body 200 of the microneedle applicator 1. A microneedle 153 to be inserted into skin is formed on a lower surface of the microneedle base 151. The cartridge 100 is replaced when the drug infusion by the microneedle 153 is fully completed.

The microneedle applicator 1 is provided with a pressing portion 404 to press one microneedle base 151 toward the patient's skin. Accordingly, the microneedle 153 is inserted into the skin, and a drug is infused.

The microneedle 153 may be produced in one of a hollow type in which a drug is infused through a hollow of the needle, a coated type in which a drug is applied to the surface of the needle and is dissolved in the skin, and a dissolving type in which the microneedle itself is composed of a drug component and is dissolved in skin.

A display unit is formed on an upper surface of the microneedle applicator, and a variety of information, such as the state of the microneedle applicator, is displayed. Also, preferably, the display unit is provided as a touchscreen to enable a user to manipulate the microneedle applicator by touching the surface of the display unit.

In this embodiment, the pressing portion 404 is operated by the interaction of a driving source 402, which is a motor, and a power transfer unit 403, which is a gear. The microneedle applicator is equipped with a rechargeable or replaceable battery to operate the driving source 402 or supply electricity to a necessary part.

The pressing portion 404 of this embodiment not only moves toward skin (to a lower side in FIG. 5) but also rotates on an upper side of the cartridge 100 with respect to a shaft 450 to press the microneedle base 151 on the cartridge 100 one by one.

Figure 5:
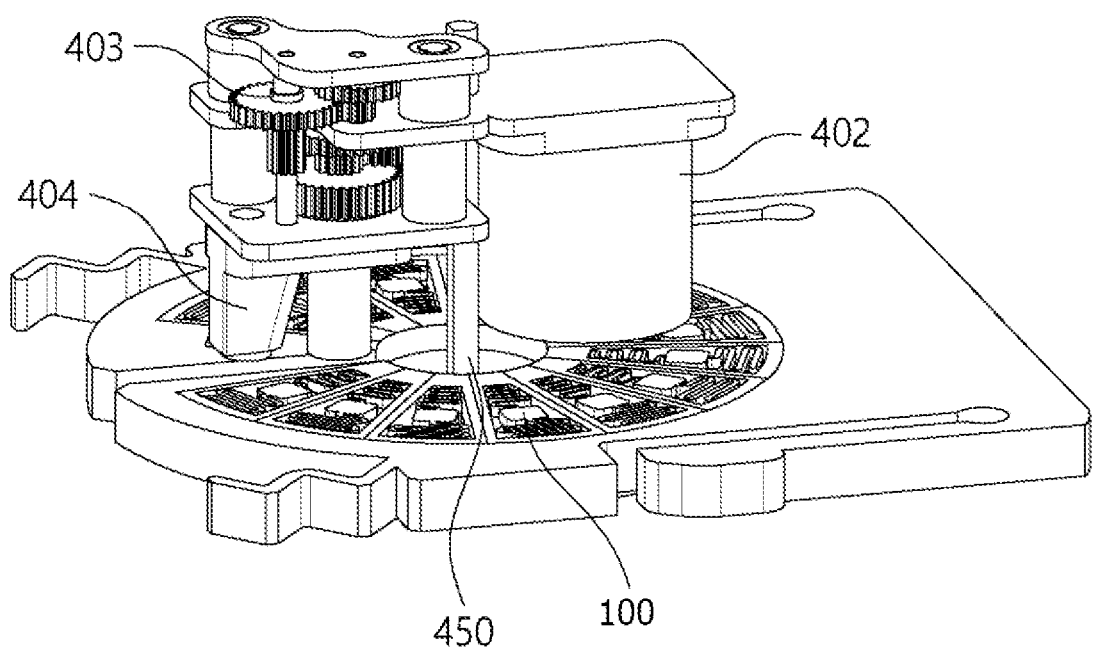
FIG. 5 is a view illustrating an operation relationship of a microneedle applicator according to an embodiment of the present disclosure.
Figure 6:
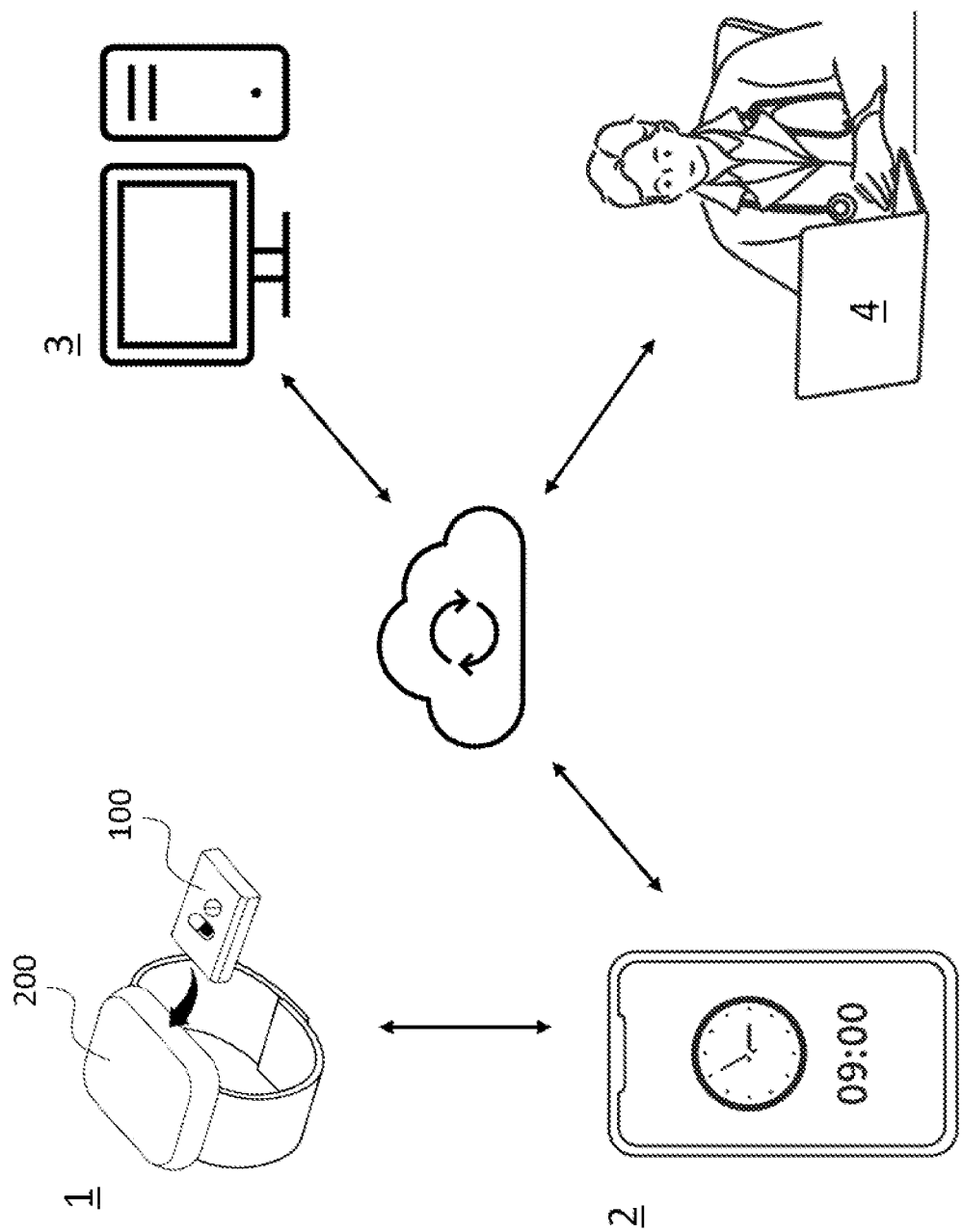
FIG. 6 is a view showing a drug compliance management system according to an embodiment of the present disclosure.
Figure 7:
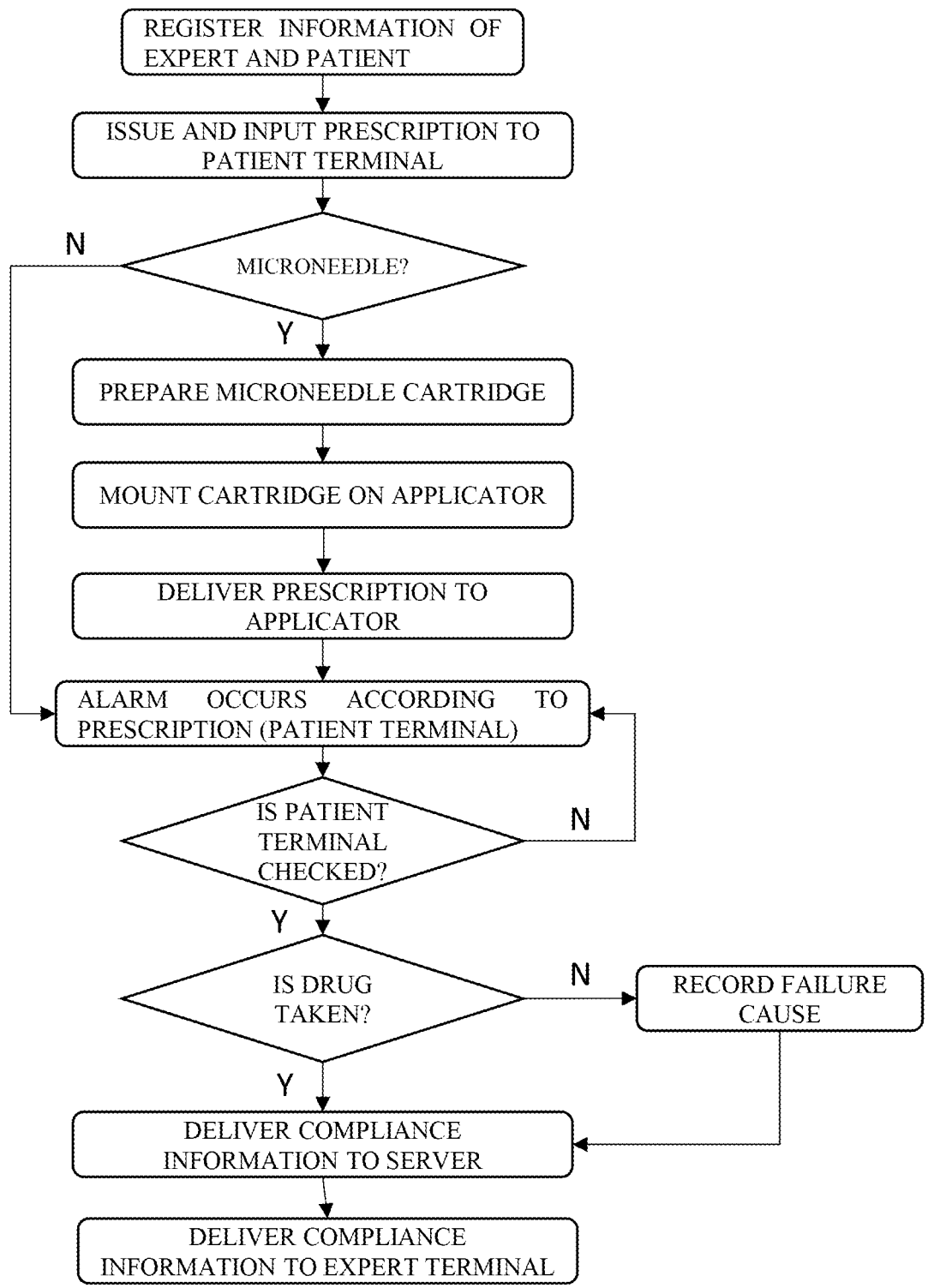
FIG. 7 is a flowchart illustrating a drug compliance management method according to an embodiment of the present disclosure.

Unlike the case of FIG. 5 in which the pressing portion 404 rotates, the pressing portion 404 does not rotate but moves up and down toward skin, and instead, the cartridge 100 may rotate.

The upper and lower surfaces of the cartridge 100 are covered with a thin film made of a material such as metal or synthetic resin, and each through hole 150 is sealed by the thin film adhered along the circumference of the through hole 150 of the cartridge 100. The sealing can prevent contamination of the microneedle.

Thereafter, when the upper surface of the microneedle base 151 is pressed by the pressing portion 404, the microneedle 153 on the lower surface of the microneedle base 151 tears a thin film and is inserted into skin.

The microneedle base 151 is disposed in each through hole 150 of the cartridge 100. The microneedle base 151 is connected to an inner wall of the through hole 150 by connection members 157 and 159. The microneedle base 151 pressed to the skin by the pressing portion 404 is returned to its original position by the elastic force of the connection member 155 when the pressing portion 404 is retracted after the drug infusion. The elastic force of the connection member 155 may be obtained according to the material or shape of the connection member. In this embodiment, a connection member bent in a zigzag pattern to have an increased overall length may allow the return caused by the elastic force.

In this embodiment, although it has been described that the microneedle base 151 is returned to its original position by the elastic force of the connection member 155, the microneedle base 151 may be returned to its original position by the elastic force of the thin film attached to an upper side or a lower side of the through hole 150. That is, while upper and lower thin films are adhered to the upper surface of the microneedle base or brought in contact with the lower surface thereof, the microneedle base may be returned to its original position by its own elasticity. In this case, the connection member 155 does not need to have an elastic force and is preferably formed to be easily cut.

A disinfectant solution may be stored in some through holes of the microneedle. In this case, preferably, a microneedle installed in the through hole in which the disinfectant solution is stored is not coated with a drug, and only a sharp tip capable of piercing a thin film is provided.

The disinfectant solution stored in the through hole flows out through the hole of the thin film perforated by the microneedle and the pressing portion and disinfects the surface of skin. Then, when the cartridge rotates, a microneedle located in an adjacent through hole moves over the sterilized surface of the skin, and the microneedle is inserted by the pressing portion so that the drug can be infused.

Typically, it is known that the skin into which the microneedle is inserted is restored to its original state after about four hours, therefore damage to the skin may occur when a drug is infused again within a shorter period of time.

In order to prevent this damage, it is also preferable to form different numbers or arrangements of microneedles 153 attached to the lower surface of the microneedle base 151 to change the insertion sites.

The drug supplied into the cartridge need not be limited to only one, and various drugs may be supplied by the microneedle.

When the microneedle applicator 1 in the form of a wearable device is more adhered to skin, it is easier to insert the microneedle. In order to check the degree of such adhesion, preferably, an adhesion measurement unit is provided on the lower surface of the microneedle applicator 1. The adhesion measurement unit may be configured as an electrostatic element or a piezoelectric element to measure the degree of adhesion.

The operation of the cartridge 100 or the pressing portion 404 is controlled by a controller of the microneedle applicator 1. The controller of the microneedle applicator 1 has a function of sending or receiving various kinds of data to or from the patient terminal 2.

Data transfer between the microneedle applicator 1 and the patient terminal 2 is also possible by wire but is preferably performed by Bluetooth or NFC.

The patient terminal 2 delivers drug infusion information received from the microneedle applicator 1 to the expert terminal 4 via the server 3, and the expert may comprehensively review drug compliance for each patient or for each drug through the expert terminal 4.

The patient terminal and the expert terminal in the present disclosure may be computing devices such as a mobile phone, a smartwatch, a personal digital assistant (PDA), a notebook computer, and a desktop computer that are connected to the Internet to exchange and process information. Also, when the patient terminal is in the form of a smartwatch, the microneedle applicator and the patient terminal may be formed as one device. In this case, the microneedle applicator and the patient terminal should be understood as a part responsible for the above-described functions in one device.

The compliance management system of the above configuration of the present disclosure may be operated according to the following method.

First, patient information and expert information are registered in the server 3.

The patient information may be registered in the server 3 through the patient terminal 2 or the expert terminal 4. That is, the patient information may be registered in the server by the patient himself or herself through the patient terminal 2 or by a medical institution providing the registered patient information.

The patient information consists of the patient's name, age, and gender as essential information and may further include the patient's height and weight, the names of substances that cause an allergic reaction in the patient, and a medication history.

An expert corresponds to medical staff who treats or cares for a patient or who prescribes or produces a drug and may include various organizations that require medical information, such as health care companies, insurance companies, governments, universities, or research institutes.

In the following description, unless otherwise stated, an expert refers to medical staff.

When a prescription is issued by an expert who has treated a patient, the prescription is input to the patient terminal.

The prescription may include information on the type of drug, dosage, and the frequency and timing of medication.

A prescription from an expert may be issued in the form of a QR code or barcode, and the prescription may be input by the patient terminal scanning the QR code or barcode or may be transmitted directly from the expert terminal to the patient terminal through the server.

The patient terminal is connected to the microneedle applicator to deliver the prescription.

A QR code or barcode is printed on a cartridge prepared to load a drug according to the prescription. Accordingly, when the cartridge is mounted on the microneedle applicator, the microneedle applicator may read the QR code or barcode so that the prescription is delivered to the microneedle applicator.

The microneedle applicator that has received the cartridge and the prescription infuses the drug at predetermined times or at predetermined intervals according to the prescription.

Preferably, the microneedle applicator warns the patient by itself or through the patient terminal before the microneedle is inserted, and the pressing portion presses the microneedle base after a confirmation input is received by the patient terminal or the microneedle applicator.

The warning to the patient may be a vibration or beep sound generated by the microneedle applicator or the patient terminal.

Before infusing the drug, a site into which the microneedle is to be inserted may be disinfected by the disinfectant solution stored in the cartridge.

A disinfectant solution is stored in some of a plurality of through-holes that are sealed at the top and bottom, and when a thin film of a through hole in which the disinfectant solution is stored is perforated by the microneedle, the disinfectant solution flows into a microneedle insertion site and disinfects the surface of skin.

The result of infusing the drug as described above is stored in the controller of the microneedle applicator 1 and then is delivered to the patient terminal 2 at predetermined intervals or upon the request from the patient terminal 2.

Meanwhile, in addition to drug infusion by the microneedle, a patient may have to take medication orally or through a patch according to a separate prescription. In this case, the patient's medication information may be input through the patient terminal 2 or by delivering a prescription input from the expert terminal 4 to the patient terminal 2.

When the medication information consisting of the type, dose, and medication cycle of a drug is input, the patient should take the drug according to an alarm that notifies the patient terminal 2 and should input, to the patient terminal 2, whether the drug was actually taken after the medication.

However, the drug infusion by the microneedle may fail for reasons such as discharge of the battery of the microneedle applicator, non-attachment of the microneedle applicator to the human body, or the exhaustion of the drug in the cartridge.

Also, the medication may fail because another drug, instead of an originally prescribed drug, has to be taken due to another disease or because a drug cannot be taken after an alarm provided by the patient terminal at a set time is ignored.

The failure of infusion or medication administration directly affects drug compliance information, and the reasons for the failure are stored in the patient terminal 2 automatically or according to the patient's input.

Preferably, both of the failure and reason for the drug infusion or medication administration are stored in the drug compliance information.

The drug compliance information, which consists of information on the infusion of a drug by microneedle collected by the patient terminal and medication information corresponding to a separate prescription, is delivered to a server periodically or upon a request from the patient terminal.

The server delivers the drug compliance information to an expert terminal periodically or upon a request from the expert terminal.

An expert who has reviewed drug compliance information of each patient through the expert terminal may send instructions for taking medication to the patient terminal through the server if necessary. For drugs with low drug compliance, the drug compliance information can be used to adjust the dosage or cycle by adjusting the dosage form or concentration.

Also, the expert terminal exchanges messages with the patient terminal through a chatting window, and thus the expert can check a patient's condition and provide a consultation or prescription for remote treatment.

According to the above configuration of the present disclosure, it is possible to accurately manage drug compliance with respect to drug infusion by a patient or an expert such as medical staff when a drug is periodically or repeatedly infused through a microneedle.

It is also possible to allow a failure cause or the like to be recorded and stored when drug infusion or medication administration fails and thus allow measures to be established.

It is also possible to prevent infection of an insertion site due to the repeated insertion of a microneedle.

The elements of the exemplary device, system, and method employed in accordance with the above embodiments may be composed, at least in part, of digital electronic circuits, analog electronic circuits, or computer hardware, firmware, software, or a combination thereof, and the elements may be executed or operably controlled by a computer program, program code, or instruction.

The description of the embodiments is provided for the purpose of illustrating the principles of the present disclosure and its practical application, thereby enabling those skilled in the art to understand the present disclosure having various embodiments and various modifications.

The disclosed embodiments are not intended to limit the present disclosure, and one of the embodiments and/or elements disclosed herein may be combined with each other to form various additional embodiments not specifically disclosed. Accordingly, additional embodiments are possible and intended to be included within the scope of this disclosure and the present disclosure.

What is claimed is:

1. A drug compliance management method comprising:
   registering information on a patient and an expert in a server;
   issuing and inputting the expert's prescription to a patient terminal;
   preparing a cartridge including a plurality of through holes, a micro-needle base positioned in each of the through holes, and a microneedle formed on a lower surface of a microneedle base to deliver a drug according to the prescription;
   mounting the cartridge on a microneedle applicator;
   delivering the prescription from the cartridge or the patient terminal to the microneedle applicator;
   enabling a pressing portion of the microneedle applicator to operate every predetermined time according to the prescription to insert the microneedle into skin and infuse a drug;
   delivering a result of infusing the drug from the microneedle applicator to the patient terminal;
   when there is a separate prescription other than the prescription for the microneedle, inputting a type, a dose, and a medication cycle of a drug to be taken to the patient terminal according to the separate prescription and inputting whether to take medication according to the medication cycle;
   delivering, to the server, drug compliance information including infusion information of the drug infused by the micro-needle and collected by the patient terminal and medication information corresponding to the separate prescription;
   allowing the server to deliver the drug compliance information delivered from the patient terminal to an expert terminal; and
   allowing the expert terminal to classify and display drug compliance on the basis of the same drug.

2. The drug compliance management method of claim 1, wherein when the infusion of the drug fails, a controller of the microneedle applicator transmits a cause of the failure to the patient terminal, inputs the cause through the patient terminal when the patient does not take the drug according to the separate prescription, and adds the cause to the drug compliance information.

3. The drug compliance management method of claim 1, wherein the information of the patient includes the patient's name, age, and gender as essential information and may optionally include the patient's height and weight, the names of substances that cause an allergic reaction in the patient, and a medication history.

4. The drug compliance management method of claim 1, wherein a disinfectant solution is stored in some of a plurality of through holes in which the top and bottom are sealed by a thin film and in which the microneedle base is disposed, and when the thin film of the through hole in which the disinfecting solution is stored is damaged by the microneedle, the disinfecting solution flows out to a site where the microneedle is inserted.

5. The drug compliance management method of claim 1, wherein the microneedle is pressed after the degree of adhesion to the skin is checked by an adhesion measurement unit of the microneedle applicator.

6. The drug compliance management method of claim 1, further comprising allowing the microneedle applicator to notify the patient of the start of insertion either by itself or through the patient terminal before the microneedle is inserted.

7. The drug compliance management method of claim 1, wherein the microneedle base is pressed after a notification confirmation input is input to the patient terminal or the microneedle applicator.

* * * * *